(12) United States Patent
Habert-Ortoli et al.

(10) Patent No.: US 6,447,996 B1
(45) Date of Patent: Sep. 10, 2002

(54) GALANIN RECEPTORS, NUCLEIC ACIDS, TRANSFORMED CELLS AND USES THEREOF

(75) Inventors: Estelle Habert-Ortoli, Paris; Brigitte Amiranoff, Morsang sur Orge; Isabelle Loquet, Antony, all of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 08/693,308

(22) PCT Filed: Feb. 14, 1995

(86) PCT No.: PCT/FR95/00172
§ 371 (c)(1),
(2), (4) Date: Aug. 15, 1996

(87) PCT Pub. No.: WO95/22608
PCT Pub. Date: Aug. 24, 1995

(30) Foreign Application Priority Data

Feb. 17, 1994 (FR) .............................. 94 01808

(51) Int. Cl.$^7$ ..................... C12Q 1/68; C12P 21/06; C07H 21/04; C07K 1/00
(52) U.S. Cl. ..................... 435/6; 435/7.21; 435/69.1; 435/70.1; 435/320.1; 435/325; 435/361; 530/350; 536/23.5; 935/11; 935/22; 935/66; 935/109; 935/110
(58) Field of Search .................. 530/350; 536/23.1, 536/23.5, 24.3, 24.31, 24.33, 24.5; 435/6, 7.1, 7.2, 7.21, 7.32, 7.31, 41, 69.1, 70.1, 71.1, 325, 361, 243, 320.1; 935/11, 22, 66, 109, 110

(56) References Cited

FOREIGN PATENT DOCUMENTS

| EP | 514 361 | 5/1992 |
|----|---------|--------|
| WO | WO 92/15015 | 9/1992 |
| WO | WO 94/00590 | 1/1994 |

OTHER PUBLICATIONS

Stryer, L. "Biochemistry" by W.H. Freeman and Company, San Francisco, 1981 pp. 14–16 and 512.*
Lebo et al, "Cold Spring Harbor Symposia on Quantitative Biology" by Cold Spring Harbor Laboratory, 1986 pp. 169–176.*
Chen et al, Proc. Natl. Acad. Sci., 90:3845–3849, May 1993.*
Nicholl et al, Genomics, 30:629–630, 1995.*
Wynick et al, Proc. Natl. Acad. Sci, 90:4231–4235, May 1993.*
Amiranoff et al, J. Biol. Chem, 264(34):20714–20717, 1989.*
Hulting et al, Brain Research, 625:173–176, 1993.*
Hulting et al., Galanin receptors from human pituitary tumors assayed with human galanin as ligand, Brain Research, 625, 173–176 (1993).
Bartfai et al., Galanin–receptor ligand M40 peptide distinguishes between putative galanin–receptor subtypes., Proc. Natl. Acad. Sci., USA vol. 90, 11287–11291 (1993).
Laburthe et al., Receptors for gut regulatory peptides, Bailliere's Clinical Endocrinology & Metabolism, vol. 8, No. 1, 77–110 (1994).
Amiranoff et al., Galanin Receptor in the Rat Pancreatic β Cell Line Rin m 5F, The Journal of Biological Chemistry, vol. 264, No. 34, 20714–20717 (1989).
Chen et al., Purification of a galanin receptor from pig brain, Proc. Natl. Acad. Sci. USA, vol. 90, 3845–3849 (1993).
Habert–Ortoli et al., Molecular cloning of a functional human galanin receptor, Proc. Natl. Acad. Sci. USA, vol. 91, 9780–9783 (1994).

* cited by examiner

*Primary Examiner*—Patricia A. Duffy
(74) *Attorney, Agent, or Firm*—F. Aaron Dubberley (57) ABSTRACT

Polypeptides having galanin receptor activity, genetic material for expressing same, any recombinant cell expressing said polypeptides, and the use thereof, are disclosed.

26 Claims, 3 Drawing Sheets

GALANIN RECEPTORS, NUCLEIC ACIDS, TRANSFORMED CELLS AND USES THEREOF

The present invention relates to new polypeptides and to the genetic material permitting their expression. More especially, it relates to new polypeptides having galanin receptor activity.

Galanin is a ubiquitous neuropeptide of 29 amino acids in mammals (30 in man) which controls miscellaneous biological functions, namely (i) endocrine secretions (insulin, somatostatin, glucagon, growth hormone, etc.), (ii) muscle tone in the digestive tract, (iii) control of behaviour (food intake, perception of painful stimuli, learning, memory, pain, etc.), through a neuromodulatory effect at central nervous system level. This non-exhaustive list of the effects of galanin, most often demonstrated in animals, explains the growing interest of pharmacologists in this neuropeptide. Selective molecules (galanin agonist or antagonist) would constitute potential pharmacological agents in endocrinology, neurology and psychiatry (Bartfai et al., (1992) TIPS 13, 312–317).

A study of the mechanism of action of galanin shows that it acts via specific membrane receptors. The biochemical and molecular characterization of the receptor (Chen et al., (1993) PNAS 90, 3845–3849, Fisone et al., (1989) Eur. J. Biochem. 180, 269–276) indicates that it belongs to the family of receptors coupled to G proteins. Depending on the target tissues, the peptide inhibits adenylate cyclase, decreases intracellular calcium, blocks voltage-dependent calcium channels or activates ATP-sensitive potassium channels. Studies of structure-activity relationships, by means of C- and N-terminal fragments of galanin and of chimeric peptides, have shown that (1) irrespective of the tissue, no partial sequence of the peptide is sufficient for obtaining full activity, (2) depending on the tissues, the first two N-terminal amino acids and the C-terminal domain 16-29 of galanin are not always essential for its activity. These observations suggest the existence of subtypes of galaninergic receptors.

The present invention describes for the first time the cloning of a gene coding for a human galaninergic receptor. The present invention also describes for the first time the sequence of galaninergic receptors and their expression in recombinant cells. The present invention thus permits a better understanding of the structure of the galaninergic receptors and enables their mechanism of action to be studied more meticulously. The present invention also enables galaninergic receptors of very high purity to be obtained in large amounts, enabling functional and pharmacological studies, the production of antibodies, and the like, to be carried out. The invention also makes it possible to prepare fragments of galaninergic receptors of defined size, as well as all kinds of derivatives of galaninergic receptors. The invention also provides recombinant cells expressing galaninergic receptors or fragments of galaninergic receptors, which are usable for the screening of ligands for these receptors (agonists, antagonists, modulators, and the like). The DNA sequences of the invention also make it possible to produce probes capable of detecting any irregularity in the expression of a galaninergic receptor (non-expression, mutation, polymorphism, and the like) in biological samples. These probes can also be used for the cloning by hybridization of any other cDNA coding for a galaninergic receptor, from tissues of diverse origins, as indicated later.

Hence a first subject of the invention lies in a nucleotide sequence coding for a polypeptide having galaninergic receptor activity. For the purposes of the invention, galaninergic receptor comprises, in particular, all the potential subtypes.

More preferably, the nucleotide sequence according to the invention is chosen from:
(a) all or part of the nucleotide sequence SEQ ID No. 1 or of its complementary strand,
(b) any sequence hybridizing with a sequence (a) and coding for a polypeptide having galaninergic receptor activity, and
(c) the sequences derived from the sequences (a) and (b) as a result of the degeneracy of the genetic code.

A very special embodiment of the invention is represented by a nucleotide sequence comprising all or part of the nucleotide sequence SEQ ID No. 1 or of its complementary strand.

The different nucleotide sequences of the invention may be of artificial origin or otherwise. They can be genomic, cDNA or RNA sequences, hybrid sequences or synthetic or semi-synthetic sequences. These sequences may be obtained, for example, by the screening of DNA libraries (cDNA library, genomic DNA library) by means of probes produced on the basis of the sequence SEQ ID No. 1. Such libraries may be prepared from cells of different origins by standard techniques of molecular biology known to a person skilled in the art. The nucleotide sequences of the invention may also be prepared by chemical synthesis, in particular according to the phosphoramidite method, or alternatively by mixed methods including the chemical or enzymatic modification of sequences obtained by the screening of libraries.

The nucleotide sequences of the invention may be used for the production of galaninergic polypeptides. The term galaninergic polypeptide denotes any polypeptide having galaninergic receptor activity, and any fragment or derivative of such a polypeptide. For the production of galaninergic polypeptides, the portion coding for the said polypeptide is generally placed under the control of signals permitting its expression in a cell host. The choice of these signals (promoters, terminators, and the like) may vary in accordance with the cell host used. To this end, the nucleotide sequences of the invention may form part of a vector, which can be autonomously replicating or integrative. More especially, autonomously replicating vectors may be prepared using sequences which are autonomously replicating in the chosen host. As regards integrative vectors, these may be prepared, for example, using sequences which are homologous to certain regions of the host's genome, permitting integration of the vector by homologous recombination. The cell hosts which can be used for the production of the galaninergic polypeptides of the invention by methods employing recombination are either eukaryotic or prokaryotic hosts. Among suitable eukaryotic hosts, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, COS, CHO, C127, NIH-3T3, and the like, cells may be mentioned. Among fungi, Aspergillus ssp. or Trichoderma ssp. may be mentioned more especially. As prokaryotic hosts, it is preferable to use the following bacteria: *E.coli*, Bacillus or Streptomyces.

The nucleotide sequences of the present invention can also be used in the pharmaceutical field, either for the production of antisense sequences which can be used in the context of a gene therapy, or for the production of probes permitting the detection, by hybridization experiments, of the expression of galaninergic receptors in biological samples and the demonstration of genetic abnormalities (polymorphism, mutations) or of aberrant expressions.

The inhibition of the expression of certain genes by antisense sequences has proved to be a promising strategy in the control of the activity of a gene. Antisense sequences are sequences whose transcription product is complementary to the coding strand of a given gene and is, as a result, capable of hybridizing specifically with the transcribed mRNA or with the gene, inhibiting its transcription or its translation into protein. Thus, a subject of the invention is the antisense sequences capable of at least partially inhibiting the production of galaninergic polypeptides as are defined above. Such sequences can consist of all or part of the nucleotide sequences defined above. They are generally sequences or fragments of sequences complementary to sequences coding for peptides of the invention. Such sequences may be obtained from the sequence SEQ ID No. 1, by fragmentation, and the like, or by chemical synthesis.

As mentioned above, the invention also makes it possible to produce nucleotide probes, synthetic or otherwise, capable of hybridizing with the nucleotide sequences defined above which code for galaninergic polypeptides of the invention, or with the corresponding mRNAs. Such probes may be used in vitro as a diagnostic tool for detecting the expression of a galaninergic receptor, or alternatively for demonstrating genetic abnormalities (incorrect splicing, polymorphism, point mutations, and the like). In view of the large number of activities of the endogenous ligands for the galaninergic receptors, the probes of the invention may thus enable neurological, cardiovascular, endocrinological or psychiatric disorders to be identified. These probes may also be used for demonstrating and isolating homologous nucleic acid sequences coding for galaninergic polypeptides as are defined above, from other cellular sources and preferably from cells of human origin. Although the present application is illustrated more especially by a clone designated GalR1, the biochemical and immunological studies described in the literature indicate the existence of subtypes of galaninergic receptors. The probes of the invention enable these different subtypes to be isolated by techniques known to a person skilled in the art (see Example 4). The probes of the invention generally contain at least 10 bases, and they can contain up to the whole of the sequence SEQ ID No. 1 or of its complementary strand. Preferably, these probes are labelled prior to their use. For this purpose, different techniques known to a person skilled in the art may be employed (radioactive labelling, enzyme labelling, and the like). The hybridization conditions under which these probes may be used are indicated in the general cloning techniques below, as well as in the examples.

A subject of the invention is also any polypeptide resulting from the expression of a nucleotide sequence as defined above. Preferably, it is a polypeptide comprising all or part of the peptide sequence SEQ ID No. 2 or of a derivative of the latter.

For the purposes of the present invention, the term derivative denotes any molecule obtained by modification of a genetic and/or chemical nature of the peptide sequence SEQ ID No. 2. Modification of a genetic and/or chemical nature may be understood to mean any mutation, substitution, deletion, addition and/or modification of one or more residues. Such derivatives may be generated for different purposes, such as, in particular, that of increasing the affinity of the peptide for its ligand(s), that of improving its levels of production, that of increasing its resistance to proteases, that of increasing and/or modifying its activity or that of endowing it with new pharmacokinetic and/or biological properties. Among the derivatives resulting from an addition, chimeric polypeptides containing an additional heterologous portion linked to one end may be mentioned as an example. The term derivative also comprises polypeptides homologous to the polypeptide SEQ ID No. 2 originating from other cellular sources, and in particular from cells of human origin, or from other organisms, and possessing an activity of the same type. Such homologous polypeptides comprise, in particular, the different subtypes of galaninergic receptors. They may be obtained, in particular, by hybridization experiments as described in the examples.

Preferably, the polypeptides of the invention are polypeptides possessing the capacity to bind galanin or a variant of galanin. Still according to a preferred embodiment, the polypeptides of the invention are capable of being recognized by antibodies that recognize the complete peptide sequence SEQ ID No. 2. Such antibodies may be generated by any technique known to a person skilled in the art, using the polypeptides described in the present application as antigens.

As indicated in the examples, these polypeptides may be expressed in different cell types to form functional galaninergic receptors.

The polypeptides of the invention may be obtained by expression in a cell host of a nucleotide sequence as described above, by chemical synthesis on the basis of the sequence SEQ ID No. 2 using techniques known to a person skilled in the art, or by a combination of these techniques.

Another subject of the invention relates to recombinant cells capable of expressing at their surface a polypeptide having galaninergic receptor activity. These cells may be obtained by introducing a nucleotide sequence as defined above, and then culturing the said cells under conditions for expression of the said sequence.

The recombinant cells according to the invention can be either eukaryotic or prokaryotic cells. Among suitable eukaryotic cells, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, COS, CHO, C127, NIH-3T3, and the like, cells, may be mentioned. Among fungi, Aspergillus ssp. or Trichoderma ssp. may be mentioned more especially. As prokaryotic cells, it is preferable to use the following bacteria: *E.coli,* Bacillus or Streptomyces. The cells thereby obtained may be used to measure the capacity of different molecules to behave as a ligand for the galaninergic receptors or as a modulator of the activity of these receptors. More especially, they may thus be used in a method for demonstrating and isolating ligands for the galaninergic receptors or modulator of the activity of these receptors, and more preferably agonists and antagonists.

Hence another subject of the invention relates to a method for demonstrating and/or isolating ligands for the galaninergic receptors, according to which the following steps are carried out:

a molecule or a mixture containing different molecules, where appropriate unidentified, is brought into contact with a recombinant cell as described above expressing at its surface a polypeptide having galaninergic receptor activity, under conditions permitting interaction between the said polypeptide and the said molecule in the case where the latter were to possess an affinity for the said polypeptide, and the molecules bound to the said polypeptide are detected and/or isolated.

In a particular embodiment, this method of the invention is adapted to the demonstration and/or isolation of agonists and antagonists of galanin for the galaninergic receptors.

Another subject of the invention relates to a method for demonstrating and/or isolating modulators for the galaninergic receptors, according to which the following steps are carried out:

a molecule or a mixture containing different molecules, where appropriate unidentified, is brought into contact with a recombinant cell as described above expressing at its surface a polypeptide having galaninergic receptor activity, in the presence of the endogenous ligand for the said receptor, under conditions permitting interaction between the said polypeptide and its ligand, and the molecules capable of modulating the activity of the ligand with respect to the said polypeptide are detected and/or isolated.

In a particular embodiment, this method of the invention is adapted to the demonstration and/or isolation of modulators of the activity of galanin with respect to the galaninergic receptors.

Another subject of the invention relates to the use of a ligand or a modulator identified and/or obtained according to the method described above, as a medicinal product. Such ligands or modulators can, in effect, enable certain disorders associated with the galaninergic receptors to be treated. In particular, since the galaninergic receptors are mediators of an analgesic effect, the agonists for these receptors may be used to decrease pain sensations. Other activities of the galaninergic receptors have been mentioned in the introduction.

The invention also relates to any medicinal product comprising as active principle at least one molecule which acts on a receptor of the invention. Preferably, the molecule is a ligand or a modulator identified and/or isolated according to the method described above.

Other advantages of the present invention will become apparent on reading the examples which follow, which are to be regarded as illustrative and non-limiting.

GENERAL CLONING TECHNIQUES

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol-chloroform extraction of proteins, ethanol or isopropanol precipitation of DNA in a saline medium, transformation in *Escherichia coli*, and the like are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

To carry out ligation, the DNA fragments are separated according to their size by agarose or acrylamide gel electrophoresis, extracted with phenol or with a phenol-chloroform mixture, precipitated with ethanol and then incubated in the presence of phage T4 DNA ligase according to the supplier's recommendations.

The filling in of 5' protruding ends is performed with the Klenow fragment of *E.coli* DNA polymerase I according to the supplier's specifications. The destruction of 3' protruding ends is performed in the presence of phage T4 DNA polymerase used according to the manufacturer's recommendations. The destruction of 5' protruding ends is performed by a controlled treatment with S1 nuclease.

In vitro site-directed mutagenesis using synthetic oligodeoxynucleotides is performed according to the method developed by Taylor et al. [Nucleic Acids Res. 13 (1985) 8749–8764].

The enzymatic amplification of DNA fragments by the so-called PCR [Polymerase-catalysed Chain Reaction, Saiki R. K. et al., Science 230 (1985) 1350–1354; Mullis K. B. and Faloona F. A., Meth. Enzym. 155 (1987) 335–350] technique.

Verification of the nucleotide sequences is performed by the method developed by Sanger et al. [Proc. Natl. Acad. Sci. USA, 74 (1977) 5463–5467].

For the hybridization experiments, the stringency conditions are based on Maniatis T. et al., cited above.

EXAMPLE 1

Isolation of the Human Galanin Receptor

This example describes the isolation of the clone GalRI coding for the human galanin receptor, by screening by expression of a cDNA library.

1a. Construction of the Library

A CDNA library was produced from the Bowes human melanocyte line (ATCC® CRL 9607) using the mammalian transient expression vector pcDNA1. After extraction of the total RNAs, the polyA$^+$ RNAs are purified on an oligodT-cellulose column. The synthesis of cDNA is performed in the presence of a mixture of primers (oligodT and oligonucleotides hybridizing at random). After a fractionation by size (>1100 base pairs), the library was constructed by ligating the cDNAs in the vector pcDNA1 (Bstx1 cloning sites) and transformation in *E. Coli* (MC 1061/P3). $10_6$ independent clones were obtained and amplified. Approximately 720000 bacterial clones were then cultured on selective solid medium at a density of 8000 colonies per dish. 90 batches of plasmid DNA, each corresponding to 8000 colonies, were prepared by alkaline lysis.

1b. Transfection

The plasmid DNA from each batch was transfected independently into Cos1 cells (ATCC® CRL 1650) by electroporation according to the following protocol: 32 mg of DNA, $8 \times 10^6$ cells in 500 ml of DMEM (Dulbecco Modified Eagle Medium) supplemented with 10% of foetal calf serum, 6 mM glutamine, 100 IU/ml of penicillin and 100 mg/ml of streptomycin under 5% CO2, 960 mF, 250 volts, Biorad electroporator. After electroporation, the cells were cultured in monolayers in culture dishes (Nunc) 16 cm in diameter for 72 hours. Under these conditions, an average of 30% of cells were transfected.

1c. Screening by Expression

The transfected cells were tested for their capacity to bind [$^{125}$I]galanin. 48 hours after transfection, the cells were changed. On the day of binding, they are placed in the presence of DMEM for 1 hour and then washed with 10 ml of buffer 1 (25 mM Tris-HCl pH 7.5, 10 mM MgCl2, 2% BSA). The cells were then incubated for 5 hours at 20° C. in the presence of buffer 2 (buffer 1 containing a cocktail of protease inhibitors: 10 mg/ml of aprotinin, 1 mg/ml of bacitracin, 10 mg/ml of pepstatin A and $10^{-5}$M phenyl-methylsulphonyl fluoride) containing $10^{-10}$M [$^{125}$I]galanin (NEN, porcine galanin 1–29, SA: 2200 curie/mmol). After washing (5×15 ml of buffer 1), the dishes were dried and exposed in autoradiography (Amersham hyperscreen MP film) for 15 days at −80° C.

1d. Isolation of the Clone GalR1 Coding for the Galanin Receptor

Of the 720000 bacterial clones tested, one batch of 8000 colonies giving a specific signal in autoradiography (i.e. (i) exceeding the background, (ii) disappearing in the presence of $10^{-6}$M cold galanin) was identified. This batch was then divided into 48 batches of 700 clones each. After transfection, the cells were tested for their capacity to bind [$^{125}$I]galanin. Three batches produce a specific signal in autoradiography. One of them was subdivided twice (25 batches of 30 clones, then 60 individual clones), leading to 2 clones endowing Cos1 cells with a strong capacity to bind [$^{125}$I]galanin.

EXAMPLE 2
Structural Study of the Galanin Receptor

The 2 clones isolated in Example 1 contain an identical insert of 3.1 kb. The sequence of one of the 2 clones was determined on both strands, by the fluorescent technique (Applied Biosystems) derived from Sanger's method, using Taq polymerase and fluorescent dideoxynucleotides.

The sequence obtained corresponds to the sequence SEQ ID No. 1. It carries an open reading frame of 1053 base pairs: the translation initiation site is assigned to the ATG codon at position 787 of the sequence SEQ ID No. 1.

The open reading frame thus defined codes for a protein of 349 amino acids (SEQ ID No. 2) of calculated molecular weight 38897 daltons. Analysis of the hydrophaticity profile of the amino acid sequence suggests that the receptor possesses 7 segments consisting of predominantly hydrophobic amino acids, globally forming transmembrane segments (TMS), a point common to the members of the family of receptors coupled to G proteins. The receptor is organized as follows: MET1-ASN33, N-terminal segment; PHE34-LEU58, TMS I; ALA59-ASN71, intracellular loop I; LEU72-LEU98, TMS II; PRO99-LYS109, extracellular loop I; PHE110-ASP132, TMSIII; ARG133-ASN151, intracellular loop II; ALA152-VAL170, TMS IV; ALA171-ALA199, extracellular loop II; TYR200-VAL223, STMV; LEU224-LYS244, intracellular loop III; THR245-LEU268, TMS VI; TRP269-PRO279, extracellular loop III; ALA280-SER307, TMS VII; GLU308-VAL349, C-terminal segment.

Furthermore, some amino acids conserved within the members of the family of receptors coupled to G proteins are present in the protein sequence of the GALR1 receptor. In particular, (1) 2 N-glycosylation sites (ASN7 and ASN12), (2) 1 site of phosphorylation by cAMP- or cGMP-dependent protein kinase (SER143), (3) 1 farnesylation site (CYS340), (4) 2 cysteines (CYS187 and 308), (5) 4 prolines (PRO169, 212,262 and 300), (6) the motif GLY.ASN.X.X.VAL (50–54), (7) the motif ASP.ARG.TYR (132–134) and (8) the motif ASN.PRO.ILE.X.TYR (299–303) are noted.

The sequence of the protein of the present invention was finally compared with the sequences of the proteins of the family of receptors coupled to G proteins (Swissprot data data bank). The largest homology (33.8% including 3 gaps) is observed with the type 4 somatostatin receptor.

EXAMPLE 3
Biochemical Studies of the GalR1 Receptor Expressed Transiently in Cos1 Cells 3a. Stoichiometry and Pharmacology of the GalR1 Receptor The plasmid DNA of the clone GalR1 was prepared by standard techniques of molecular biology for transfecting Cos1 cells. The membranes of the transfected cells were then used to estimate the parameters of equilibrium binding of galanin 1-29 and of galanin fragments.

The plasmid DNA (90 mg/8×10$^6$ Cos1 cells) was transfected by electroporation as described above (1b). 72 hours after transfection, the recombinant cells were harvested and sedimented. The membranes were then prepared as follows: at 4° C., the cell pellet is placed in the presence of 10 ml of buffer 3 (5 mM Hepes pH 7.5) for 20 minutes; after centrifugation at 13,000 g for 15 minutes, the pellet is resuspended in buffer 3 and stored at −80° C. until used.

Equilibrium binding experiments (saturation and competition) were carried out on the membranes in the presence of [$^{125}$I]galanin and of different peptides under the following experimental conditions: the membranes (10 mg of protein) were incubated for 30 minutes at 20° C. with 5×10$^{-11}$M [$^{125}$I]galanin in the absence or presence of increasing concentrations of galanin 1-29, galanin 2-29, galanin 3-29 or galanin 1-16 ($10^{-11}$M–$10^{-6}$M), in a final volume of 0.25 ml of buffer 2 (1c). The reaction was then stopped by adding 0.25 ml of buffer 1 (1c) and centrifugation for 15 minutes at 13000 g. The pellet obtained was washed three times with 0.2 ml of ice-cold 25 mM Tris buffer (pH 7.5) containing 10% of sucrose, and the radio-activity was then measured with a gamma scintillation counter. Non-specific binding is measured in the presence of $10^{-7}$M porcine galanin 1-29. The values of the affinity constants (Ki) were obtained according to the equation of Cheng and Prussof: Ki=IC50/(1+L/Kd).

Figure 1:
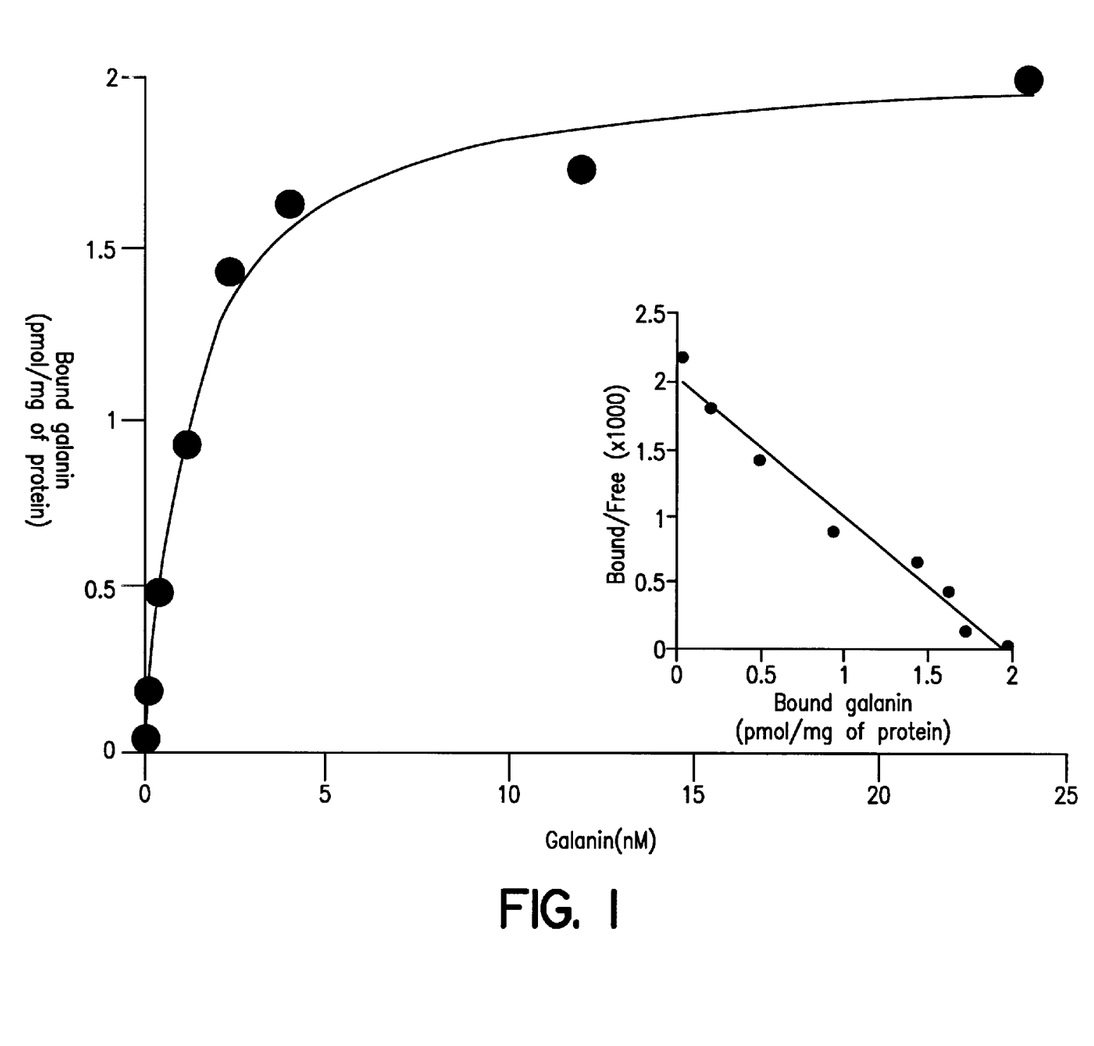
FIG. 1: Saturation of galanin receptors with porcine galanin, on membranes of Cos1 cells transfected with the clone GalR1. The inset represents the Scatchard plot of the binding curve data (The values presented correspond to a representative experiment in which each point was determined in triplicate).

Under the experimental conditions described above, the following results are observed: in contrast to untransfected Cos1 cells or Cos1 cells transfected with a control plasmid, Cos1 cells transfected with the clone GalR1 display a specific binding of iodinated galanin. Analysis of the results by Scatchard's method shows the existence of a single class of sites of high affinity, with an apparent dissociation constant (Kd)=0.8 nM, and of high capacity, with a maximum number of binding sites (Bmax)=2.8 pmol/mg protein. Taking into account the efficiency of transfection (approximately 30%, 1b), the level of expression of galaninergic receptors of the invention in Cos1 cells is estimated at 5×10$^5$ sites/cell.

Figure 2:
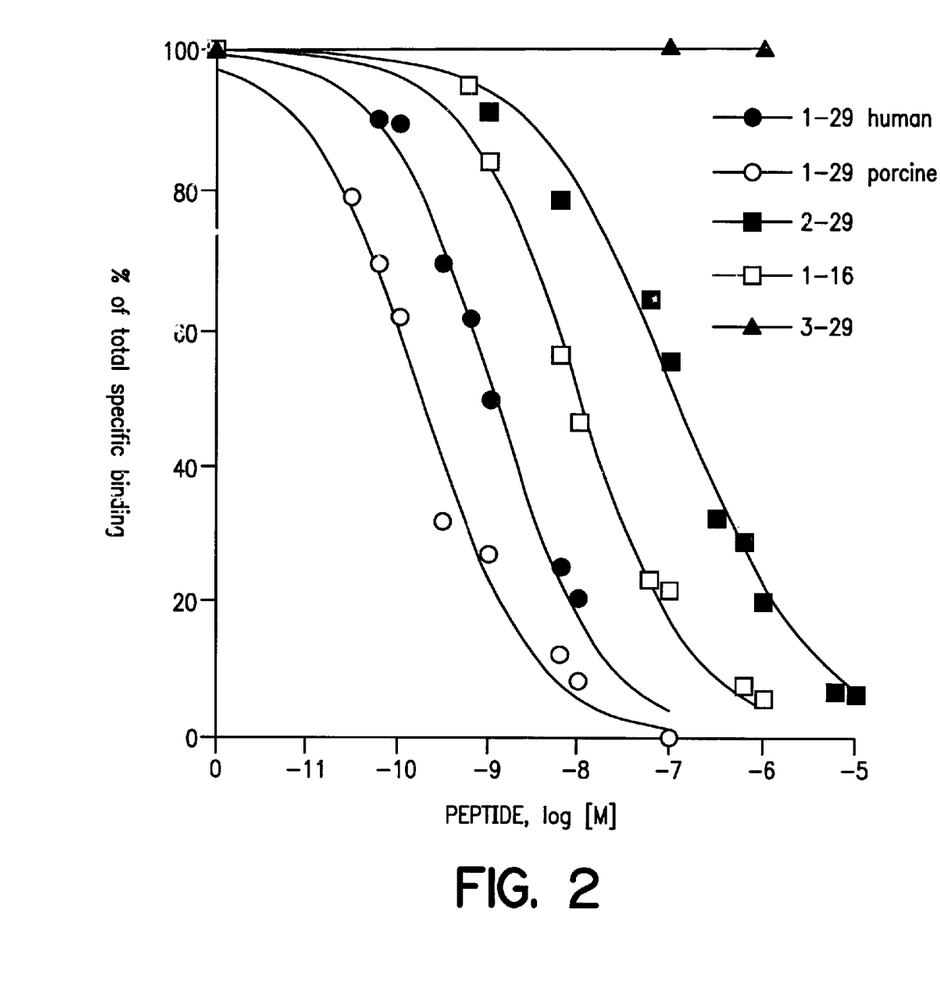
FIG. 2: Displacements by peptides of the specific binding of [$^{125}$I]galanin to membranes of Cos1 cells transfected with the clone GalR1. (The values presented correspond to a representative experiment in which each point was determined in triplicate).

Rat, porcine and human galanins inhibit competitively the binding of [$^{125}$I]galanin to the membranes of the transfected cells, with a Ki=0.3, 0.2 and 0.8 nM, respectively. Galanin 2-29 (Ki=115 nM) and galanin 1-16 (Ki=5 nM) inhibit competitively the binding of [$^{125}$I]galanin with a lower affinity than galanin 1-29. This clone does not have affinity for galanin 3-29.

The order of efficiency of these different molecules confirms the specificity of the GalR1 receptor as a galaninergic receptor. These results show, moreover, that the Cos1 cells of the present invention are capable of expressing the receptor for galanin having binding characteristics comparable to those of the native receptor.

3b. Functional Study of the GalR1 Receptor

The coupling of the galanin receptor to adenylate cyclase was estimated by the capacity of galanin to inhibit cAMP production in Cos1 cells transfected with the clone GalR1. For this study, $10^5$ cells transfected under the conditions described above were inoculated into multiwell (diameter 1.5 cm) culture plates, and the cAMP experiments were carried out 72 hours after transfection (the culture medium is renewed on the day before the experiment). After a preincubation for 1 hour at 37° C. in DMEM medium, the cells were washed with DMEM containing 2% of BSA. They were then incubated for 30 minutes at 37° C. in this same medium containing $2 \times 10^{-4}$M isobutylmethylxanthine, in the absence and presence of forskolin ($10^{-4}$M) and/or of human galanin ($10^{-11}$M–$10^{-6}$M). After three washes of the cells in DMEM medium, the intracellular cAMP is extracted by adding 70% ethanol. After lyophilization, the cAMP is measured by radioimmunology (cAMP Kit, Amersham).

Figure 3:
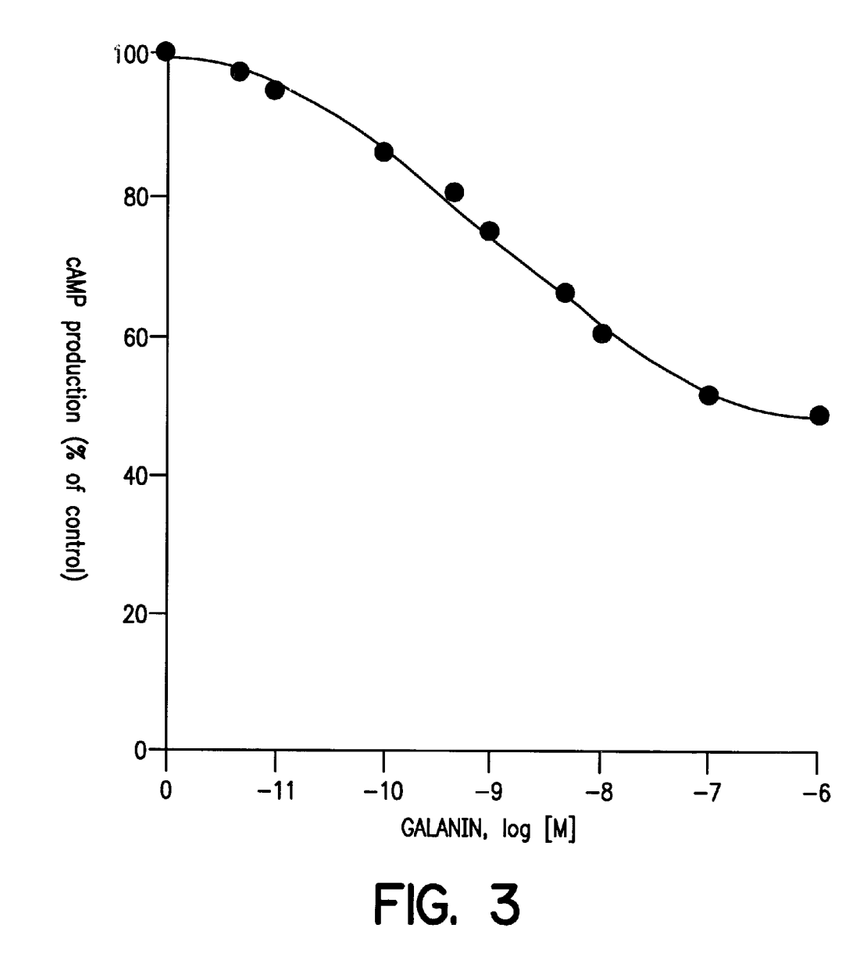
FIG. 3: Inhibition by galanin of the stimulation of cAMP production in Cos1 cells transfected with the clone GALR1 (The values presented correspond to a representative experiment in which each point was determined in duplicate).

The results show that, in Cos1 cells transfected with the clone GalR1, galanin strongly inhibits the forskolin-induced production of intracellular cAMP (the induced production is of the order of 2 pmol/$10^5$ cells, that is to say 10 times the basal level). This effect is not observed under basal conditions. The half-inhibition and the maximum inhibition of cAMP production are induced by $10^{-9}$M and $10^{-6}$M human galanin, respectively. In the presence of $10^{-6}$M galanin, the forskolin-induced production of intracellular cAMP is decreased by 50%.

The inhibition by galanin of forskolin-induced production of intracellular cAMP confirms the specificity of the GalR1 receptor as a galaninergic receptor. These results show, moreover, that the Cos1 cells of the present invention are capable of expressing the receptor for galanin having functional characteristics comparable to those of the native receptor.

EXAMPLE 4

Searches for Homologous Sequences, in Particular for Subtypes, in Other Tissues

This example shows that the nucleotide sequence SEQ ID No. 1 or fragments of the latter may be used for the demonstration of homologous sequences, in particular of subtypes, from other tissues. For this purpose, different techniques can be used, such as PCR, in situ hybridization, Northern transfer, and the like.

More especially, for investigation using PCR, the total RNAs of the different tissues studied are prepared and then subjected to reverse transcription and to an amplification, in the presence of reverse transcriptase, Taq polymerase and suitable primers derived from the sequence SEQ ID No. 1. The products thereby obtained are then transferred onto nitrocellulose filters and hybridized under variable conditions of stringency.

The homologous sequences demonstrated in these experiments may then be isolated and/or amplified by standard techniques of molecular biology.

What is claimed is:

1. An isolated nucleic acid having a sequence selected from the group consisting of:
   (a) a double-stranded nucleotide sequence as depicted by SEQ ID No. 1, and
   (b) a nucleotide sequence which encodes a polypeptide having amino acid sequence SEQ ID No. 2.

2. An isolated nucleic acid comprising the double-stranded nucleotide sequence as depicted by SEQ ID No. 1.

3. An isolated nucleic acid, which is RNA corresponding to SEQ ID No. 1.

4. A vector comprising an isolated nucleic acid having a nucleotide sequence encoding a galanin receptor polypeptide selected from the group consisting of:
   (a) the double-stranded nucleotide sequence as depicted by SEQ ID No. 1, and
   (b) a nucleotide sequence which encodes a polypeptide having an amino acid sequence SEQ ID No. 2,
wherein the nucleic acid is under the control of signals permitting its expression in a cell host.

5. A recombinant cell comprising the vector according to claim 4, wherein the cell expresses a polypeptide having galaninergic receptor activity at its surface.

6. The recombinant cell according to claim 5, wherein the cell is eukaryotic.

7. The recombinant cell according to claim 6, wherein the cell is an animal cell.

8. The vector according to claim 4 which is autonomously replicating.

9. A recombinant cell comprising the vector according to claim 8, wherein the cell expresses a polypeptide having galaninergic receptor activity at its surface.

10. The recombinant cell according to claim 9, wherein the cell is eukaryotic.

11. The recombinant cell according to claim 10, wherein the cell is an animal cell.

12. The vector according to claim 4 which is integrative.

13. A recombinant cell comprising the vector according to claim 12, wherein the cell expresses a polypeptide having galaninergic receptor activity at its surface.

14. The recombinant cell according to claim 13, wherein the cell is eukaryotic.

15. The recombinant cell according to claim 14, wherein the cell is an animal cell.

16. A method for expressing a galaninergic receptor comprising culturing a cell containing the vector of claim 4 under conditions that permit expression of galaninergic receptor encoded by the vector.

17. A method for detecting a nucleic acid encoding a galaninergic receptor polypeptide comprising contacting the nucleic acid with an isolated nucleotide probe having a nucleotide sequence of SEQ ID No. 1 and detecting hybridization of the probe with the nucleic acid, wherein hybridization indicates that the nucleic acid codes for a galaninergic receptor polypeptide.

18. An isolated polypeptide comprising the amino acid sequence of SEQ ID No. 2.

19. An isolated polypeptide encoded by a nucleic acid having a nucleotide sequence encoding a galanin receptor polypeptide selected from the group consisting of (a) a double-stranded nucleotide sequence as depicted by SEQ ID No. 1, and (b) a nucleotide sequence which encodes a polypeptide having amino acid sequence SEQ ID No. 2.

20. A method for demonstrating a ligand for a galaninergic receptor, wherein the method comprises (a) contacting a molecule or a mixture containing different molecules with the recombinant cell expressing a polypeptide having galaninergic receptor activity at its surface according to claim 6, under conditions permitting interaction between the polypeptide and the molecule wherein the latter possesses an affinity for the polypeptide, and (b) detecting the molecules specifically bound to the polypeptide, wherein such a molecule is a ligand.

21. The method for demonstrating a ligand for a galaninergic receptor as in claim 20, wherein the ligand is an agonist of galanin for the galaninergic receptor.

22. The method for demonstrating a ligand for a galaninergic receptor as in claim 20, wherein the ligand is an antagonist of galanin for the galaninergic receptor.

23. The method for demonstrating a ligand for a galaninergic receptor according to claim 20, wherein the method further comprises isolating the ligand.

24. A method for demonstrating a modulator for a galaninergic receptor, wherein the method comprises (a) contacting a molecule or a mixture containing different molecules with the recombinant cell according to claim 5 under conditions permitting interaction between the polypeptide having galaninergic receptor activity and galanin, and (b) detecting the molecule that is able to modulate the activity of galanin with respect to the polypeptide.

25. The method for demonstrating a modulator for a galaninergic receptor according to claim 24, wherein the method further comprises isolating the modulator.

26. The method according to claim 25, wherein the modulator is able to inhibit competitively the binding of galanin with respect to the galaninergic receptor.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3083 base pairs
      (B) TYPE: nucleic acid
      (C) STRANDEDNESS: double
      (D) TOPOLOGY: linear    (ii) MOLECULE TYPE: cDNA    (iii) HYPOTHETICAL: NO    (iv) ANTI-SENSE: NO    (vi) ORIGINAL SOURCE:
      (A) ORGANISM: Homo sapiens    (ix) FEATURE:
      (A) NAME/KEY: CDS
      (B) LOCATION: 787..1836

(xi) SEQUENCE DESCRIPTION: SEQ ID NO:1:

```
ATTCGGCGGC GACCCATCCC GCTAGAATCC GTCCAGTCTC TGCTCGCGCA CCGTGACTTC     60

TAAGGGGCGC GGATTTCAGC CGAGCTGTTT TCGCCTCTCA GTTGCAGCAG AGAAGCCCCT    120

GGCACCCGAC TCTATCCACC ACCAGGAAGC CTCCCAAAAG AGCTCTCGCC CTGTGGACGA    180

CTCGGAATCC CTGGAAAAGC CGGGAGGGAG TCGGAGGCGC CAGCCCACTG GGGAGGTGGC    240

GCTGGGCGCG CGGGATGCGC GGGGAGCCTT CTCTGCAGGA GCCGCACAGT GCACTGCTGC    300

GCGCTGGGCA GTGCGGGGAA GCGCCGCGGG AAGGAGCGGC TCCGAGCAAC AGGTGCAGCA    360

CGCAGCCGCT CCGGGAGCCA GGGAAAACCG CCGGCGAAGA TCTGGAGCGG TAAGGCGGAG    420
```

```
AGAAGGGTCT TTCCACCTGC GCGGCTGCAG CCGGCGGATC CCTCTTCCCA GGCTCCGTGG      480

TCGCGCAGCG GGCGGAGGCG CCCGGGCAGG GGACCCCAGT GCTCTCGAGA TCACCGTCCC      540

TTCCCGAGAA GGTCCAGCTC CGGGCTCCCG AACCCACCCT CTCTCAGAAG GTCGCGGCGC      600

AAAGACGGTG CCACCAGGCA CGGCCACCGG ATCCCCGCTC CCGCTGGCTC GCGCCTCGGG      660

GGAAGCTCAG ACTCCTAAAC TCGCACTCTC CGTGCTTTGC GCCGGGACCC CTGGCCACCC      720

CCGGCGCCTG CTATCCCGCC CTCCCTCCCG CGCGCTCCGC CGCTCGCCGG GACAGCCCCG      780

CGGGCC ATG GAG CTG GCG GTC GGG AAC CTC AGC GAG GGC AAC GCG AGC         828
       Met Glu Leu Ala Val Gly Asn Leu Ser Glu Gly Asn Ala Ser
        1               5                  10

TGT CCG GAG CCC CCC GCC CCG GAG CCC GGG CCG CTG TTC GGC ATC GGC         876
Cys Pro Glu Pro Pro Ala Pro Glu Pro Gly Pro Leu Phe Gly Ile Gly
 15              20              25                  30

GTG GAG AAC TTC GTC ACG CTG GTG GTG TTC GGC CTG ATC TTC GCG CTG         924
Val Glu Asn Phe Val Thr Leu Val Val Phe Gly Leu Ile Phe Ala Leu
                 35              40              45

GGC GTG CTG GGC AAC AGC CTA GTG ATC ACC GTG CTG GCG CGC AGC AAG         972
Gly Val Leu Gly Asn Ser Leu Val Ile Thr Val Leu Ala Arg Ser Lys
             50              55              60

CCG GGC AAG CCG CGG AGC ACC ACC AAC CTG TTC ATC CTC AAC CTG AGC        1020
Pro Gly Lys Pro Arg Ser Thr Thr Asn Leu Phe Ile Leu Asn Leu Ser
         65              70              75

ATC GCC GAC CTG GCC TAC CTG CTC TTC TGC ATC CCC TTC CAG GCC ACC        1068
Ile Ala Asp Leu Ala Tyr Leu Leu Phe Cys Ile Pro Phe Gln Ala Thr
     80              85              90

GTG TAC GCG CTG CCC ACC TGG GTG CTG GGC GCC TTC ATC TGC AAG TTC        1116
Val Tyr Ala Leu Pro Thr Trp Val Leu Gly Ala Phe Ile Cys Lys Phe
 95              100             105                 110

ATC CAC TAC TTC TTC ACC GTG TCC ATG CTG GTG AGC ATC TTC ACC CTG        1164
Ile His Tyr Phe Phe Thr Val Ser Met Leu Val Ser Ile Phe Thr Leu
                 115             120             125

GCC GCG ATG TCC GTG GAC CGC TAC GTG GCC ATC GTG CAC TCG CGG CGC        1212
Ala Ala Met Ser Val Asp Arg Tyr Val Ala Ile Val His Ser Arg Arg
             130             135             140

TCC TCC TCC CTC AGG GTG TCC CGC AAC GCG CTG CTG GGC GTG GGC TGC        1260
Ser Ser Ser Leu Arg Val Ser Arg Asn Ala Leu Leu Gly Val Gly Cys
         145             150             155

ATC TGG GCG CTG TCC ATT GCC ATG GCC TCG CCC GTG GCC TAC CAC CAG        1308
Ile Trp Ala Leu Ser Ile Ala Met Ala Ser Pro Val Ala Tyr His Gln
     160             165             170

GGC CTC TTC CAC CCG CGC GCC AGC AAC CAG ACC TTC TGC TGG GAG CAG        1356
Gly Leu Phe His Pro Arg Ala Ser Asn Gln Thr Phe Cys Trp Glu Gln
175             180             185                 190

TGG CCC GAC CCT CGC CAC AAG AAG GCC TAC GTG GTG TGC ACC TTC GTC        1404
Trp Pro Asp Pro Arg His Lys Lys Ala Tyr Val Val Cys Thr Phe Val
                 195             200             205

TTC GGC TAC CTG CTG CCG CTC CTG CTC ATC TGC TTC TGC TAT GCC AAG        1452
Phe Gly Tyr Leu Leu Pro Leu Leu Leu Ile Cys Phe Cys Tyr Ala Lys
             210             215             220

GTC CTT AAT CAC TTG CAT AAA AAG TTG AAG AAC ATG TCA AAG AAG TCT        1500
Val Leu Asn His Leu His Lys Lys Leu Lys Asn Met Ser Lys Lys Ser
         225             230             235

GAA GCA TCC AAG AAA AAG ACT GCA CAG ACA GTT CTG GTG GTG GTT GTG        1548
Glu Ala Ser Lys Lys Lys Thr Ala Gln Thr Val Leu Val Val Val Val
     240             245             250

GTG TTT GGA ATC TCC TGG CTG CCG CAC CAC ATC ATC CAT CTC TGG GCT        1596
Val Phe Gly Ile Ser Trp Leu Pro His His Ile Ile His Leu Trp Ala
```

```
                                                    -continued 255               260               265                270
GAG TTT GGA GTT TTC CCG CTG ACG CCG GCT TCC TTC CTC TTC AGA ATC    1644
Glu Phe Gly Val Phe Pro Leu Thr Pro Ala Ser Phe Leu Phe Arg Ile
                275               280               285

ACC GCC CAC TGC CTG GCG TAC AGC AAT TCC TCC GTG AAT CCT ATC ATT    1692
Thr Ala His Cys Leu Ala Tyr Ser Asn Ser Ser Val Asn Pro Ile Ile
                290               295               300

TAT GCA TTT CTC TCT GAA AAT TTC AGG AAG GCC TAT AAA CAA GTG TTC    1740
Tyr Ala Phe Leu Ser Glu Asn Phe Arg Lys Ala Tyr Lys Gln Val Phe
                305               310               315

AAG TGT CAC ATT CGC AAA GAT TCA CAC CTG AGT GAT ACT AAA GAA AAT    1788
Lys Cys His Ile Arg Lys Asp Ser His Leu Ser Asp Thr Lys Glu Asn
                320               325               330

AAA AGT CGA ATA GAC ACC CCA CCA TCA ACC AAT TGT ACT CAT GTG TGA    1836
Lys Ser Arg Ile Asp Thr Pro Pro Ser Thr Asn Cys Thr His Val  *
335               340               345               350

TAAAAGATAG AGTATCCTTA TGGTTGAGTT TCCATATAAG TGGACCAGAC ACAGAAACAA    1896

ACAGAATGAG CTAGTAAGCG ATGCTGCAAC TTGTTATCTT AACAAGAATT CAAGTCGTTT    1956

TAATTAAATC CCACGTGTGT TAAAAAGTAC TTTGATCCAT TTAGGAAATT CCTAGGTCTA    2016

GTGAGAATTA TTTTTCAATT TTATTTTAGT TCTAAATTAT GTTTCAGAAA CAAAAGACAA    2076

TGCTGTACAG TTTTATTCCT CTTCAGACAT GAAAGGGAAC ATATATATTC CATATATATG    2136

TTCAACTCTT CATAGATTGT GAGCTGGCCC ATCAATATGG TCAGGAATAT TTGCAGTCTA    2196

CATTTTAAAG CCAATTTATT TAGAAAAAAA ATTTGAGCTT TAATTCTTTA ATTTTAAGAG    2256

AAGTAATATT GTGAGCTATG TATTTTAAAA TATGATCATG GACACACAAT GATGAATTTT    2316

TTGGCCATTT ACATAGACAT ATCTATTAAG TGGAAAGAAG GCTTTCTGAA GTCTGTTTGC    2376

ACAGGTGGCA TTTGCTTCCA ATTGTAGCTA GCGCACAGAG CTTTGGAAGC CTGTCATTAT    2436

GAGATACAGT CGGTTTACCT CAGGAGTCAA TTCAGTGTTG TACTGGTGAC CTGGGATGCA    2496

GTAGTAGGCA CTGTTGATTC AAATTTATCC TGTGAAACTG GCTTTATAGA GTTAACAAAA    2556

CAGAGTCAGA GACCACTGTC TTAACAGTGG AAGATGCAAA TAAGTTTTTG AGAATAAAAC    2616

TGGATTTTGA AATTTTACAT TAGTACTTGA CAAAAGTTTT CATTTTGCCT TGAATGGAAC    2676

CTACTAAAAA GAGAGATGAA AAAAAATCAG CGAGGTTGAT GTAGATAATA ATTTCTATGG    2736

GACCAAAGAC TAGACAGAAT TCAGTAAGTC ACATGAAGTA ATGGTCATGC CTGTACATAA    2796

AGCATATTTC ATGTTTGATT TAGATGACAT TCAAAAAAAA TCATGGGACT GAATATACCT    2856

GGGGTATCCT ATCTTGTACA AATGCATGCT TTTTCATTAA ATTTGTAATG ATGTTTAATG    2916

AACATTTCCA CCAAACATTA TTTCCTCTAA AAATGTTAAT TTGGGGTTAA AACCATCACC    2976

ATTTGAATTT CAAATGTAGT TTTCATGACA ATTTTATATT GGATGTGTGT TTACAATGAG    3036

AAAATGGCAT GAAAATATTA AATTGTCTTG TATCGGAAAA GGAATTC                3083

(2) INFORMATION FOR SEQ ID NO:2:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Leu Ala Val Gly Asn Leu Ser Glu Gly Asn Ala Ser Cys Pro
1               5                   10                  15
```

-continued

```
Glu Pro Pro Ala Pro Glu Pro Gly Pro Leu Phe Gly Ile Gly Val Glu
             20                  25                  30

Asn Phe Val Thr Leu Val Val Phe Gly Leu Ile Phe Ala Leu Gly Val
             35                  40                  45

Leu Gly Asn Ser Leu Val Ile Thr Val Leu Ala Arg Ser Lys Pro Gly
     50                  55                  60

Lys Pro Arg Ser Thr Thr Asn Leu Phe Ile Leu Asn Leu Ser Ile Ala
 65              70                  75                  80

Asp Leu Ala Tyr Leu Leu Phe Cys Ile Pro Phe Gln Ala Thr Val Tyr
                 85                  90                  95

Ala Leu Pro Thr Trp Val Leu Gly Ala Phe Ile Cys Lys Phe Ile His
             100                 105                 110

Tyr Phe Phe Thr Val Ser Met Leu Val Ser Ile Phe Thr Leu Ala Ala
             115                 120                 125

Met Ser Val Asp Arg Tyr Val Ala Ile Val His Ser Arg Arg Ser Ser
     130                 135                 140

Ser Leu Arg Val Ser Arg Asn Ala Leu Leu Gly Val Gly Cys Ile Trp
145                 150                 155                 160

Ala Leu Ser Ile Ala Met Ala Ser Pro Val Ala Tyr His Gln Gly Leu
                 165                 170                 175

Phe His Pro Arg Ala Ser Asn Gln Thr Phe Cys Trp Glu Gln Trp Pro
             180                 185                 190

Asp Pro Arg His Lys Lys Ala Tyr Val Val Cys Thr Phe Val Phe Gly
             195                 200                 205

Tyr Leu Leu Pro Leu Leu Leu Ile Cys Phe Cys Tyr Ala Lys Val Leu
     210                 215                 220

Asn His Leu His Lys Lys Leu Lys Asn Met Ser Lys Lys Ser Glu Ala
225                 230                 235                 240

Ser Lys Lys Lys Thr Ala Gln Thr Val Leu Val Val Val Val Val Phe
                 245                 250                 255

Gly Ile Ser Trp Leu Pro His His Ile Ile His Leu Trp Ala Glu Phe
                 260                 265                 270

Gly Val Phe Pro Leu Thr Pro Ala Ser Phe Leu Phe Arg Ile Thr Ala
             275                 280                 285

His Cys Leu Ala Tyr Ser Asn Ser Ser Val Asn Pro Ile Ile Tyr Ala
     290                 295                 300

Phe Leu Ser Glu Asn Phe Arg Lys Ala Tyr Lys Gln Val Phe Lys Cys
305                 310                 315                 320

His Ile Arg Lys Asp Ser His Leu Ser Asp Thr Lys Glu Asn Lys Ser
                 325                 330                 335

Arg Ile Asp Thr Pro Pro Ser Thr Asn Cys Thr His Val
             340                 345
```